(12) United States Patent
Samsoondar et al.

(10) Patent No.: US 6,614,521 B2
(45) Date of Patent: Sep. 2, 2003

(54) DEVICE FOR VERIFYING THE ACCURACY OF A SPECTRAL ANALYZER

(75) Inventors: James Samsoondar, Cambridge (CA); Ashwani Kaushal, Mississauga (CA); Paul Drennan, Waterloo (CA)

(73) Assignee: CME Telemetrix Inc., Waterloo (CA)

( * ) Notice: Subject to any disclaimer, the term of this patent is extended or adjusted under 35 U.S.C. 154(b) by 0 days.

(21) Appl. No.: 10/186,274

(22) Filed: Jun. 28, 2002

(65) Prior Publication Data

US 2003/0030798 A1 Feb. 13, 2003

Related U.S. Application Data

(63) Continuation-in-part of application No. 10/085,983, filed on Feb. 28, 2002, which is a continuation of application No. PCT/CA00/01006, filed on Aug. 31, 2000.
(60) Provisional application No. 60/151,681, filed on Aug. 31, 1999.

(51) Int. Cl.[7] .................................................. G01J 7/10
(52) U.S. Cl. ...................... 356/243.1; 356/246; 600/322
(58) Field of Search .............................. 356/243.1, 244, 356/246, 39–42, 243.2, 243.4; 600/322, 323, 345, 485, 584; 128/633

(56) References Cited

U.S. PATENT DOCUMENTS

| 4,322,164 A | 3/1982 | Shaw et al. ................. 356/243 |
| 5,166,517 A | 11/1992 | Volgyesi ................... 250/252.1 |
| 5,278,627 A | 1/1994 | Aoyagi et al. ................ 356/41 |
| 5,361,758 A | 11/1994 | Hall et al. ................... 128/633 |
| 5,429,128 A | 7/1995 | Cadell et al. ................ 128/633 |
| 5,511,546 A | * 4/1996 | Hon ........................... 128/633 |
| 5,782,757 A | * 7/1998 | Diab et al. .................. 600/323 |
| 5,817,010 A | * 10/1998 | Hibl ........................... 600/344 |
| 5,860,919 A | * 1/1999 | Kian-Azarbayjany et al. ... 600/322 |
| 6,322,515 B1 | * 11/2001 | Goor et al. ................. 600/485 |
| 6,459,917 B1 | * 10/2002 | Gowda et al. .............. 600/345 |

FOREIGN PATENT DOCUMENTS

| GB | 2 280 024 A | 1/1995 |
| WO | WO 93 13706 A | 7/1993 |

* cited by examiner

Primary Examiner—Frank G. Font
Assistant Examiner—Sang H. Nguyen
(74) Attorney, Agent, or Firm—Heslin Rothenberg Farley & Mesiti P.C.

(57) ABSTRACT

An artificial member that mimics the absorbance spectrum of an animal body part and includes the spectral components of blood analytes is disclosed. The artificial member is made of a light scattering and reflecting material and is configured to be reproducibly received in a measuring receptor that is operatively connected to a non-invasive monitoring device.

29 Claims, 14 Drawing Sheets

DEVICE FOR VERIFYING THE ACCURACY OF A SPECTRAL ANALYZER

CROSS REFERENCE TO RELATED APPLICATIONS

This application is a continuation-in-part application of U.S. patent application Ser. No. 10/085,983 filed Feb. 28, 2002 as a continuation of International Patent Application Number PCT/CA00/01006 filed Aug. 31, 2000 (expired), and claims priority from U.S. Provisional Patent Application 60/151,681 filed Aug. 31, 1999 (expired). The entire contents of the prior applications is incorporated herein by reference.

FIELD OF THE INVENTION

This invention is in the field of non-invasive spectral analysis of analytes in tissues and relates more particularly to a device which may be used with a non-invasive monitoring system used for determining concentrations of various blood components.

BACKGROUND OF THE INVENTION

Non-invasive devices exist which are used externally to measure either the concentration of the constituent in gases admitted by the body or the concentrations contained in a patient's body part, typically a finger. U.S. Pat. No. 5,429,128 describes a finger receptor that receives a finger of a user and is for use with a non-invasive monitoring device, such as that described in U.S. Pat. No. 5,361,758.

During the course of using a monitoring device that is operatively coupled to a finger receptor, many uses of the receptor and the monitoring device will with time result in variations in reading due to internal drift and other variable aspects of such monitoring devices. Accordingly, it is desirable to have a means to rapidly and easily check the precision and accuracy of such a monitoring device.

SUMMARY OF THE INVENTION

The present inventors have developed a device shaped to fit a receptor that is operatively connected to a non-invasive monitoring device, which device is useful in monitoring the precision and accuracy of the non-invasive monitoring device and which permits photometric correction of the instrument.

In its broad aspect, the invention provides a method and a device made of materials for carrying out the method which reproduces absorption spectra associated with various body parts when such parts are subjected to spectral determination. A device according to the present invention is made of a material that exhibits the same light scattering and absorbency characteristics as a body part, preferably of an earlobe, lip, fold of skin or finger, most preferably, a finger.

According to one embodiment of the present invention there is provided an artificial member that mimics the absorbance spectrum of a body part and includes the spectral components of blood analytes comprising a light scattering and reflecting material, which member has a chamber portion comprising one or more chambers, the member configures to be reproducibly received in a measuring receptor that is operatively connected to a non-invasive monitoring device, preferably, the body part that is mimicked is a finger. In one embodiment, there is one chamber, while in another, there are two chambers.

In another embodiment, each chamber is filled with an O-cellulose material that mimics light scattering properties of tissue, preferably each chamber is filled with a gel material containing amaranth dye and sodium benzoate and holding light scattering and reflective particles that mimic the light scattering properties of tissue.

In another embodiment, the material that fills each chamber is fluid free. In yet another embodiment, the reflective particles comprise Teflon®-PTFE (polytetrafluoroethylene) (DuPont, Wilmington, Del., USA), titanium dioxide ($TiO_2$) or are polystyrene nanospheres.

In yet another embodiment, the light scattering and reflecting material of the member is Teflon®-PTFE, preferably the configuration of the member wherein the configuration of the member to be reproducibly received, comprises a stabilizing member extending from the chamber portion to reversibly urge other surfaces of the member into contact with the measuring receptor, preferably the stabilizing member is as depicted in FIG. 9.

In another aspect according to the present invention, there is provided a method of transferring algorithms from one spectral instrument to another, the method involving: measuring a spectral response of a member in a first spectral instrument; measuring a spectral response of the member in a second spectral instrument; determining any difference in measurements between the first instrument and the second instrument; and modifying the algorithms of the instruments to account for any difference, wherein the member of the method mimics the absorbance spectrum of a body part and includes the spectral components of blood analytes comprising a light scattering and reflecting material, which member has a chamber portion comprising one or more chambers, the member configures to be reproducibly received in a measuring receptor, that is operatively connected to a non-invasive monioring device, preferably the body part mimicked is a finger. In one embodiment of the method, there is one chamber, while in another there are two chambers.

In another embodiment of the method, each chamber is filled with an O-cellulose material that mimics light scattering properties of tissue, preferably each chamber is filled with a gel material containing amaranth dye and sodium benzoate and holding light scattering and reflective particles that mimic the light scattering properties of tissue.

In another embodiment, the material that fills each chamber is fluid free. In yet another embodiment, the reflective particles comprise Teflon®-PTFE, $TiO_2$ or are polystyrene nanospheres.

In yet another embodiment of the method. the light scattering and reflecting material of the member is Teflon®-PTFE, preferably the configuration of the member wherein the configuration of the member to be reproducibly received, comprises a stabilizing member extending from the chamber portion to reversibly urge other surfaces of the member into contact with the measuring receptor, preferably the stabilizing member is as depicted in FIG. 9.

The invention in another embodiment, provides a method for mimicking the absorbance spectrum of a body part that includes the spectral components of blood analytes, and comprises inserting a member in a measuring device operatively connected to a non-invasive monitoring device; taking measurements with the device and comparing the results with those obtained from a body part of a subject that the member is intended to mimic, wherein the member is comprised of a light scattering and reflecting material, which member is configured to be reproducibly received in the measuring receptor.

According to one embodiment of the method, the member mimics the absorbance spectrum of a body part and includes the spectral components of blood analytes comprising a light scattering and reflecting material, and the member has a chamber portion comprising one or more chambers, the member configured to be reproducibly received in a measuring receptor that is operatively connected to a non-invasive monitoring device, preferably the body part that is mimicked is a finger. In one embodiment of the method, there is one chamber, while in another there are two chambers.

In another embodiment of the method each chamber is filled with an O-cellulose material which mimics light scattering properties of tissue, preferably each chamber is filled with a gel material containing amaranth dye and sodium benzoate and holding light scattering and reflective particles which mimic the light scattering properties of tissue.

In another embodiment, the material that fills each chamber is fluid free. In yet another embodiment, the reflective particles comprise Teflon®-PTFE, $TiO_2$ or are polystyrene nanospheres.

In yet another embodiment of the method, the light scattering and reflecting material of the member is Teflon®-PTFE, preferably the configuration of the member wherein the configuration of the member to be reproducibly received, comprises a stabilizing member extending from the chamber portion to reversibly urge other surfaces of the member into contact with the measuring receptor, preferably the stabilizing member is as depicted in FIG. 9.

In another aspect, the present invention provides an artificial member that mimics the absorbance spectrum of a body part and includes the spectral components of blood analytes, the artificial member comprising a container made of a light-scattering and reflecting material, the container comprising at least one chamber, the container having a neck extending from one end thereof, the neck comprising an orifice that is sealed with a cap, the member being configured to be reproducibly received in a measuring receptor that is operatively connected to a non-invasive monitoring device.

Preferably, the member further comprises a septum that fits over the orifice and is secured by the cap. In a preferred embodiment, the septum is uniform with the cap.

In another preferred embodiment, the neck comprises a flange, and the cap is secured over the flange. In another preferred embodiment, the flange is an annular flange.

In another preferred embodiment, the cap is a crimp cap, that is preferably made of aluminum.

In another preferred embodiment, the body part, which is mimicked is a finger.

In another embodiment, the member contains one chamber, while in another it contains two chambers. Preferably, the chamber is cylindrical.

In a further embodiment, each chamber is filled with an O-cellulose material that mimics light scattering properties of tissue. Preferably, each chamber is filled with a gel material containing amaranth dye and sodium benzoate and holding light scattering and reflective particles that mimic the light scattering properties of tissue.

In another embodiment, the material that fills each chamber is fluid free. In yet another embodiment, the reflective particles comprise Teflon®-PTFE, $TiO_2$ or are polystyrene nanospheres.

In yet another embodiment, the light scattering and reflecting material of the member is Teflon®-PTFE, preferably the Teflon®-PTFE contains from about 0.1% to about 25% glass fiber. More preferably, the Teflon®-PTFE contains from about 0.1% to about 5% glass fiber.

In another preferred embodiment, the member comprises a stabilizing member extending from the chamber portion to reversibly urge other surfaces of the member into contact with the measuring receptor.

In a further aspect, the present invention provides a method for mimicking the absorbance spectrum of a body part that includes the spectral components of blood analytes, the method comprises:

(a) providing an artificial member comprising a container made of a light scattering and reflecting material, the container comprising one or more chambers, and having a neck extending from one end thereof, the neck comprising an orifice sealed with a cap, the artificial member being configured to be reproducibly received in a measuring receptor that is operatively connected to a non-invasive monitoring device;

(b) inserting the artificial member into the measuring receptor;

(c) taking measurements with the monitoring device; and (d) comparing the measurements obtained in step (c) with those obtained from a body part of a subject, which the artificial member is configured to mimic.

Preferably, the artificial member used in the method further comprises a septum that fits over the orifice and is secured by the cap. In a preferred embodiment, the septum is uniform with the cap.

Other features and advantages of me present invention win become apparent from the following detailed description, drawings and claims. It should be understood, however, that the detailed description and the specific examples while indicating preferred embodiments of the invention are given by way of illustration only, and various changes and modifications within the spirit and scope of the invention will become apparent to those skilled in the art from this detailed description.

DETAILED DESCRIPTION OF THE INVENTION

As used herein, "concentration" or "concentration level" means the amount or quantity of a constituent in a solution whether the solution is in vitro or in vivo.

As used herein, "constituent" means a substance, or analyte found in a tissue and includes carbohydrates such as, for example, glucose, bilirubin, a protein, for example, albumin or hemoglobin.

As used herein, "fluid free" means having no appreciable amount of liquid present.

As used herein, "tissue" means any tissue of the body of a subject, including for example, blood, extracellular spaces, and can mean the entire composition of a body part such as a finger or ear lobe.

As used herein, "subject" means any member of the animal kingdom including, preferably, humans.

As stated above, the present inventors have prepared a device that is capable of insertion in a receptor that is used with a non-invasive monitoring device. The use of such a device or artificial member is to enable the user of such a monitoring device to quickly and easily check the precision and accuracy of the non-invasive monitoring device.

Figure 1:
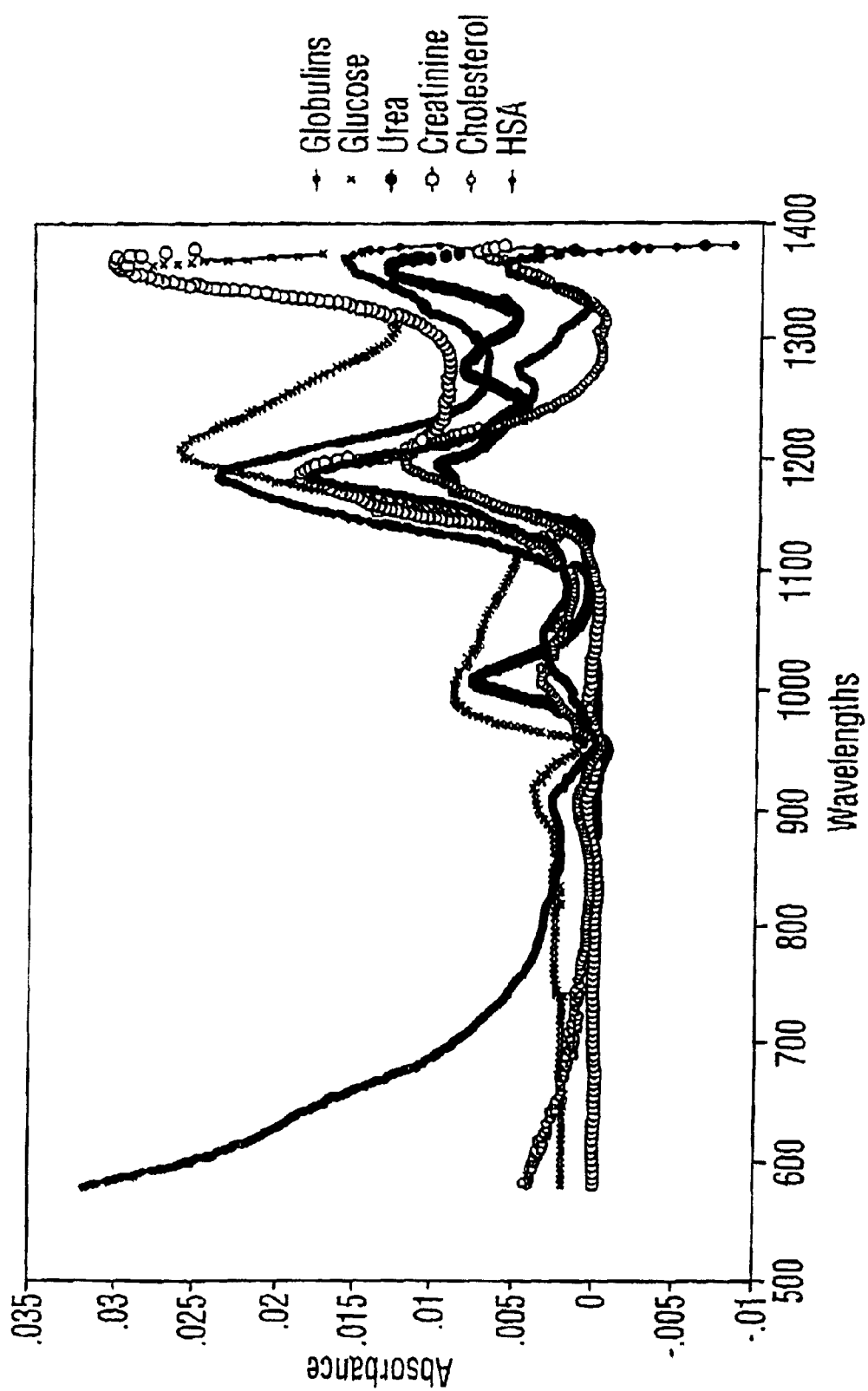
FIG. 1 shows absorbance spectra from 500–1380 nm for globulins, glucose, urea, creatinine, cholesterol and human serum albumin with water displacement compensation.

Spectral data, obtained using a standard spectrophotometer and compensated for water displacememt, were collected from in vitro measurement of a cuvette containing samples of various blood constituents, and are illustrated in FIG. 1. As may be seen, the spectra associated with the various constituents are complex. In contrast, the spectra for a living finger is relatively simple, particularly in the 500–1100 nm region. This may be seen in FIG. 2. Measurements taken in this region are relatively consistent regardless of individual measurements or the individual being scanned. In this respect. the data presented in FIG. 2 represent the combined spectra of 33 people for whom a total of 2,013 measurements were taken and collectively presented.

Figure 2:
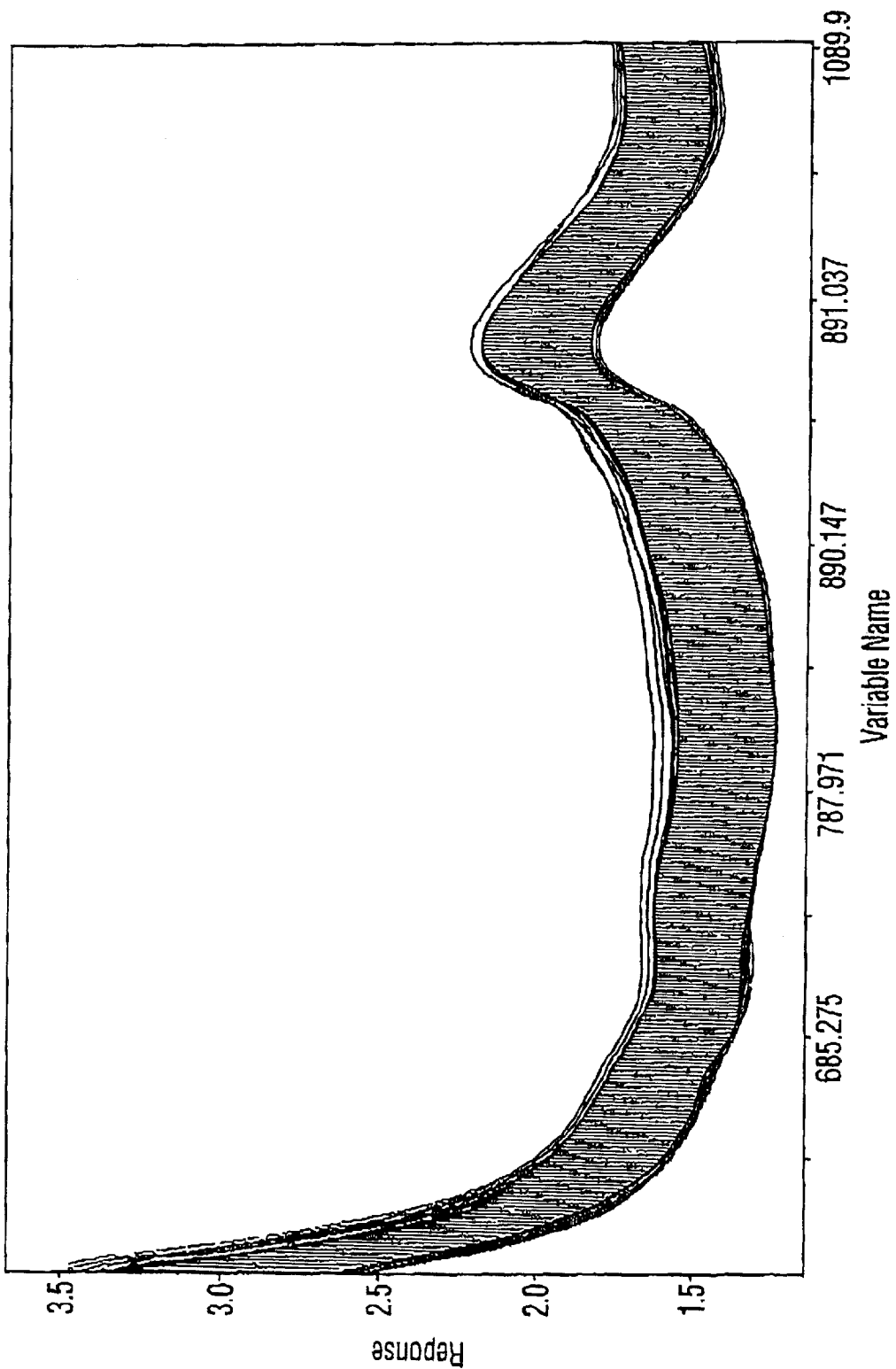
FIG. 2 shows 2013 absorbance spectra from 585–1100 nm for the finger from 32 subjects.

Accordingly, an artificial member must be able to provide a spectrum that is comparable to those presented in FIG. 2 or the absorbance spectra of another body part. It will be appreciated that in order to develop a comparable artificial member, such member must mimic the situation where light is directed to a body part. Light entering the body is scattered and that light that emerges radiates in virtually every direction. Absorption begins at the point where the light enters the tissue. In the case of transmission, as the light passes through the tissue, more and more light is absorbed as the path length increases. Clearly, if the path length is too great, very little light is left for measurement and the absorbance calculations will be subject to considerable error due to noise. These considerations are also true in respect of the artificial member.

Consequently, according to one embodiment of the present invention, it is the artificial member that will exhibit the same properties of light scattering, reflectivity and absorption as exhibited by a living human finger. Accordingly, an artificial member of the present invention is made of a highly reflective material such as, for example, Teflon®, especially Teflon®-PTFE virgin material. In addition, to concurrently mimic scatter, which is derived from the interior of a living body part, the artificial member mush show sufficient internal reflectance to achieve a comparable result. In this respect, a chamber, or container space exists in the member, although, depending on the body part being mimicked, reflective material may comprise part of the internal structure of the chamber of the member.

An artificial member must be capable of being easily inserted into and removed from a receptor that is used to measure spectral characteristics of constituents in a body part. In this respect, the shape of the artificial member will be determined by the shape of the receptor. In the case of a finger receptor, the artificial member must have corresponding shapes to ensure that there is a constant path length from the point at which light is delivered to the finger or artificial finger and the point at which light exits the finger or artificial body part.

It will be appreciated by those skilled in the art that an artificial member of the present invention is for use in association with any measuring receptor that is combined with any non-invasive monitoring device that is based on the principle of measuring the absorbance (or reflectance) of radiation passing through (or reflecting from) a body part. In this respect, such devices operate according to the Beer-Lambert law, namely that the concentration of constituents is proportional to a constant of proportionality (the extinction coefficient), the path length, and the absorbance ($LOG_{10}$ [1/T], wherein T is the transmittance, i.e., the proportion of light of a given wavelength that is transmitted through the matrix).

By measuring the absorbance at a number of predetermined wavelengths, some of which will control path length, it is possible to calculate the concentration of a given constituent. The same principles of measurement that are applied to determining concentration of constituents in body parts with a non-invasive device are equally applicable to an artificial member of the present invention.

Consequently, while water is a preferred constituent for measurement and accuracy testing with an artificial member, any other constituent, or constituents may be used. In this respect, it will be appreciated that the constituents will be preferably held in the member, preferably in the chamber or chambers of the member. In some applications, it may be necessary to introduce other absorbing or reflecting material(s) in the chamber or intermixed with the composition of the reflective material.

It should be noted that there are several ways in which absorbance measurements may be taken, and without limiting the scope of the applicability of the present invention, two such methods are: (1) using light from a scanning monochromator, pass it through a selected part of the body and collect the light transmitted through onto a silicon detector, and then measure the amount of light transmitted in the absence of the body part. With these two measurements, the transmittance, and hence the absorbance, may be calculated; and (2) using a polychromatic light source, pass it through the body part to be measured, collect the light, collimate it onto a diffraction grating and focus the different wavelengths of light on a linear array detector. Each element of the array will then measure the intensity of light for a narrow band of wavelengths (sample scan). A similar measurement in the absence of the body part (reference scan) will then allow computation of the transmittance for each element. Because various elements of the array have slightly different dark leakage currents, it is necessary to record a dark current and subtract it from both the sample scan and the reference scan before calculation of transmittance and absorbance.

There are several typical parts of the body from which measurements are mad and these include the finger, the lip, the earlobe, a pinch of skin at the waist, the web between the thumb and forefinger, and the web between the toes. Accordingly, at a minimum, the present invention includes artificial members replicating each of these body parts.

One of the problems encountered in measuring absorbance in tissue is the spectral variability from one instrument to another due to physical differences in light transmission and collection. Because the phantom finger is designed to minimize variability of spectral response and physical placement in the finger receptor, it can be used to quantify the spectral differences between instruments. With careful wavelength calibration, the difference in spectral response of the phantom finger between one instrument and another may be used to correct the spectrum of the second instrument to that of the first by adding the spectral difference to the second instrument. This is termed photometric correction and coupled with suitable wavelength accuracy, is the basis on which algorithms can be transferred from one instrument to another.

Exemplary Embodiments of the Principles of the Invention

Several non-limiting exemplary embodiments of the present invention are described below.

Figure 7:
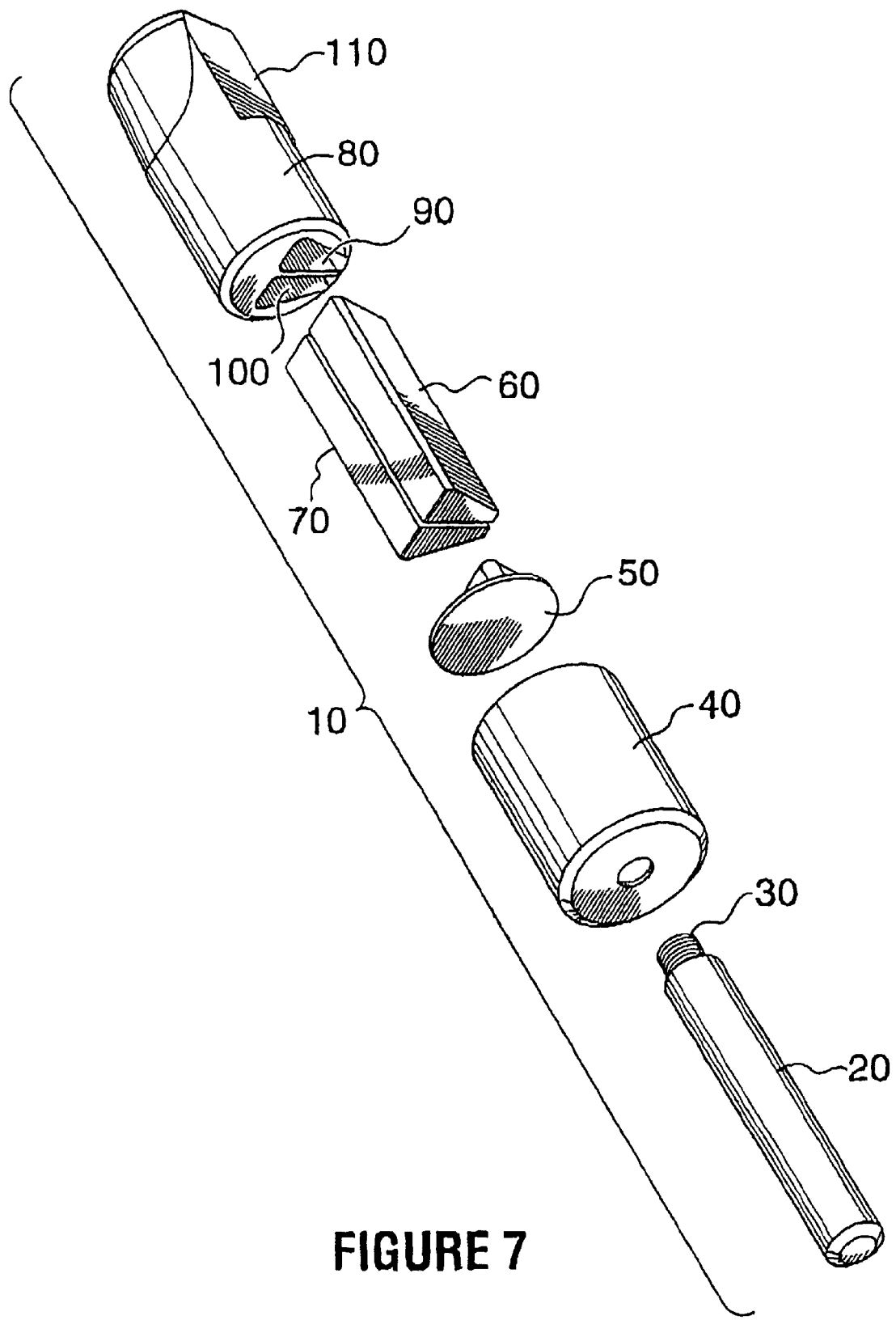
FIG. 7 is an isometric exploded view of an artificial member according to the present invention in a configuration for use with a finger receptor.
Figure 8:
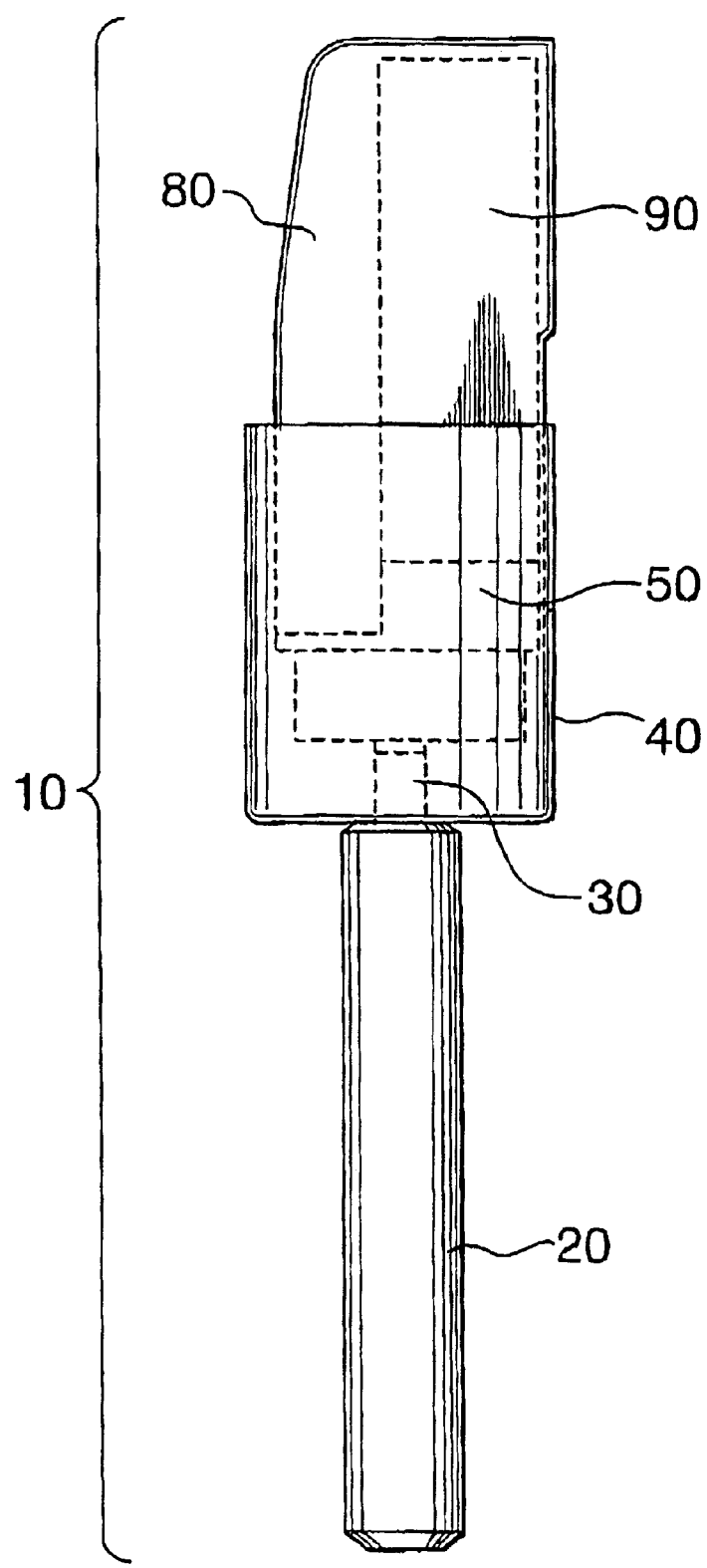
FIG. 8 is a side view of the member of FIG. 7.

First, referring to FIGS. 7 and 8, an artificial member according to the present invention is illustrated. In particular, the artificial member is intended to represent an artificial finger for use in association with a finger receptor that is operatively connected to a non-invasive monitoring device such as a spectrophotometer.

The artificial finger 10 comprises a handle 20 which may be prepared from aluminum or any other material that is rigid and has strength characteristics. The handle 20 has a tip 30 that is used to connect the handle 20 with a holding collar 40. The holding collar 40 is used to provide a large grasping means as well as a sealing cover for the highly reflective and light scattering portion 80 of the artificial finger 10.

The holding collar 40 may be made, for example, from a black plastic such as DELRIN™ (DuPont, Wilmington, Del., USA); although any other minimally reflective or non-reflective plastic material is acceptable. The holding collar 40 fits by any suitable means, for example, an interference fit over the artificial member 10. The artificial member 10 is comprised of a material that provides a scattering effect similar to tissue such as the skin or a digit. Such materials may include, for example, Teflon®-PTFE; although any other material, such as, for example, Fluorosint™ (DSM Engineering Plastic Products, Inc.) or Teflon®-PTFE comprising from about 0.1 to about 25% glass fibers, that is capable of providing such a scattering effect is suitable. The member has a hollow or chamber-like portion that determines the amount of internal scattering based on the material filling the cavity. The exact dimensions of the chamber are selected to achieve a spectrum of absorption similar to that observed of a natural finger. More than one chamber may be used.

According to a preferred embodiment, the chamber as shown in FIG. 7 is divided into two portions 90,100, although similar results may be achieved with more chambers. The chambers 90 and 100 act as containers to hold water or any other solutions that are being used as part of the artificial member. Also placed in the artificial member for the purposes of replicating absorbance of a finger are O-cello materials (commonly available as a sponge, such as, for example, SCOTCH BRITE®) that are shaped 60,70 to fit into containers 90 and 100. The chamber may also be filled with gel materials that hold light scattering materials such as $TiO_2$ or polystyrene nanospheres.

A stopper 50 made of rubber or other suitable material, is fashioned to fit into and seal the top open end of containers 90 and 100, over which holder collar 40 is placed. These parts and their interrelationship are easily seen with reference to FIG. 8, which provides a side view of the artificial finger and illustrates the various components in place. The shaping of the artificial finger in order to provide an interface between the artificial member and the receptor thereby achieving a minimum of variability and a maximum of repeatability, while allowing for the passage of light through the artificial member thereby optimizing path length and its variability between measurements with the artificial member is seen in the isometric exploded view depicted in FIG. 6 as item 110. This shaping will vary from one artificial member to another, depending upon the device in which the artificial member is being used to verify the accuracy of the spectral analyzer.

Figure 9:
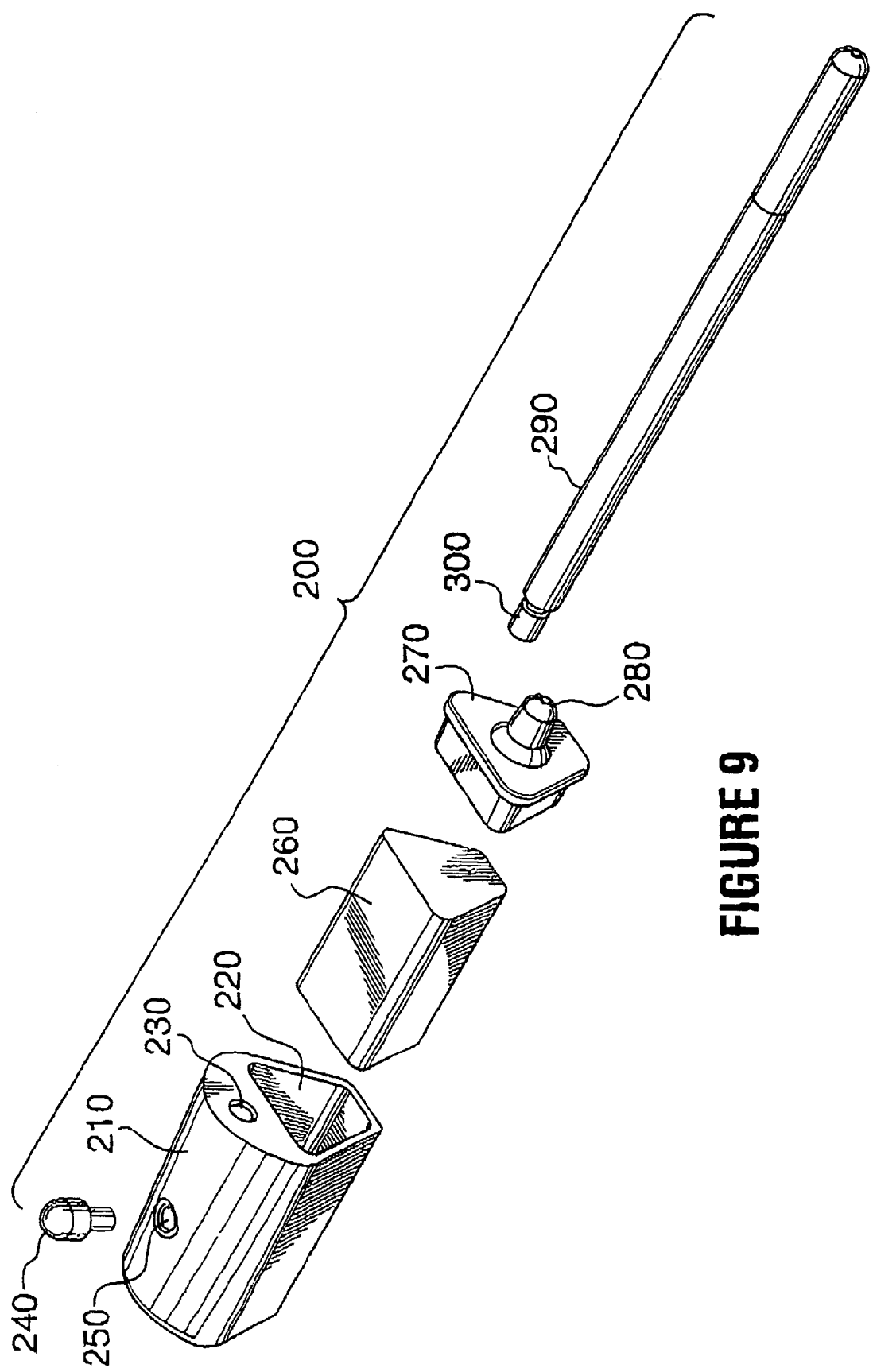
FIG. 9 is an isometric exploded view of a further embodiment of an artificial member according to the present invention in a configuration for use with a finger receptor.
Figure 10:
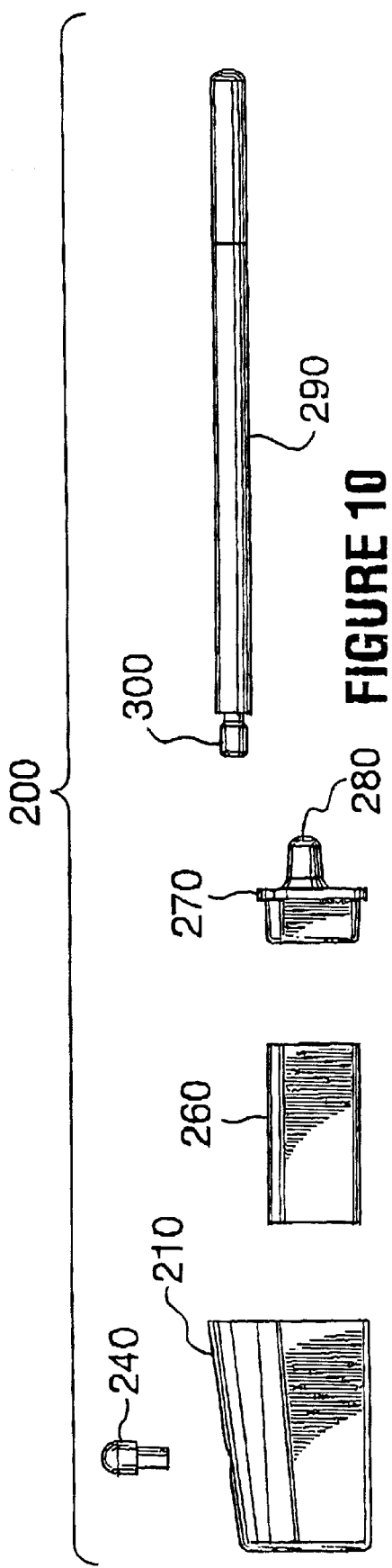
FIG. 10 is a side view of the member of FIG. 9.
Figure 11:
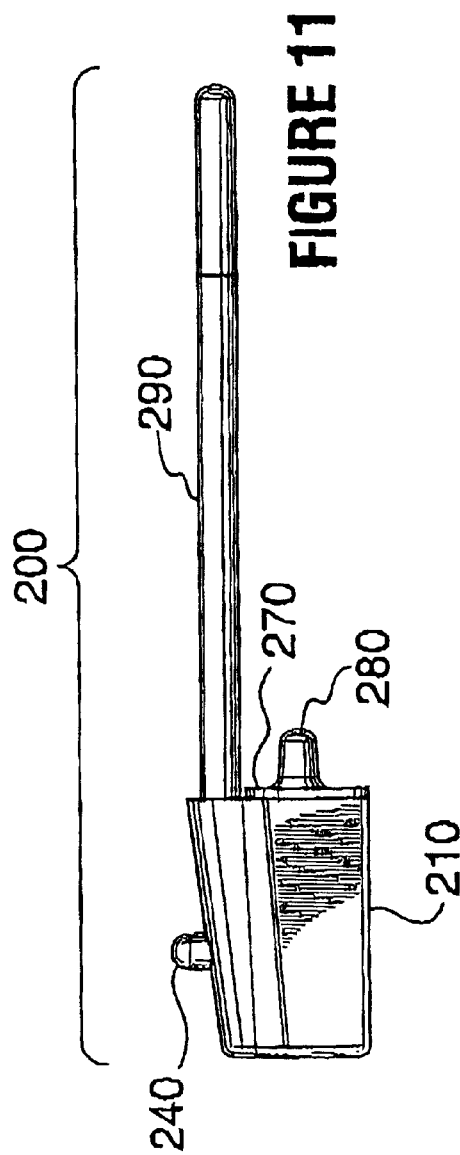
FIG. 11 is a side view of an assembled member of FIGS. 9 and 10.
Figure 15:
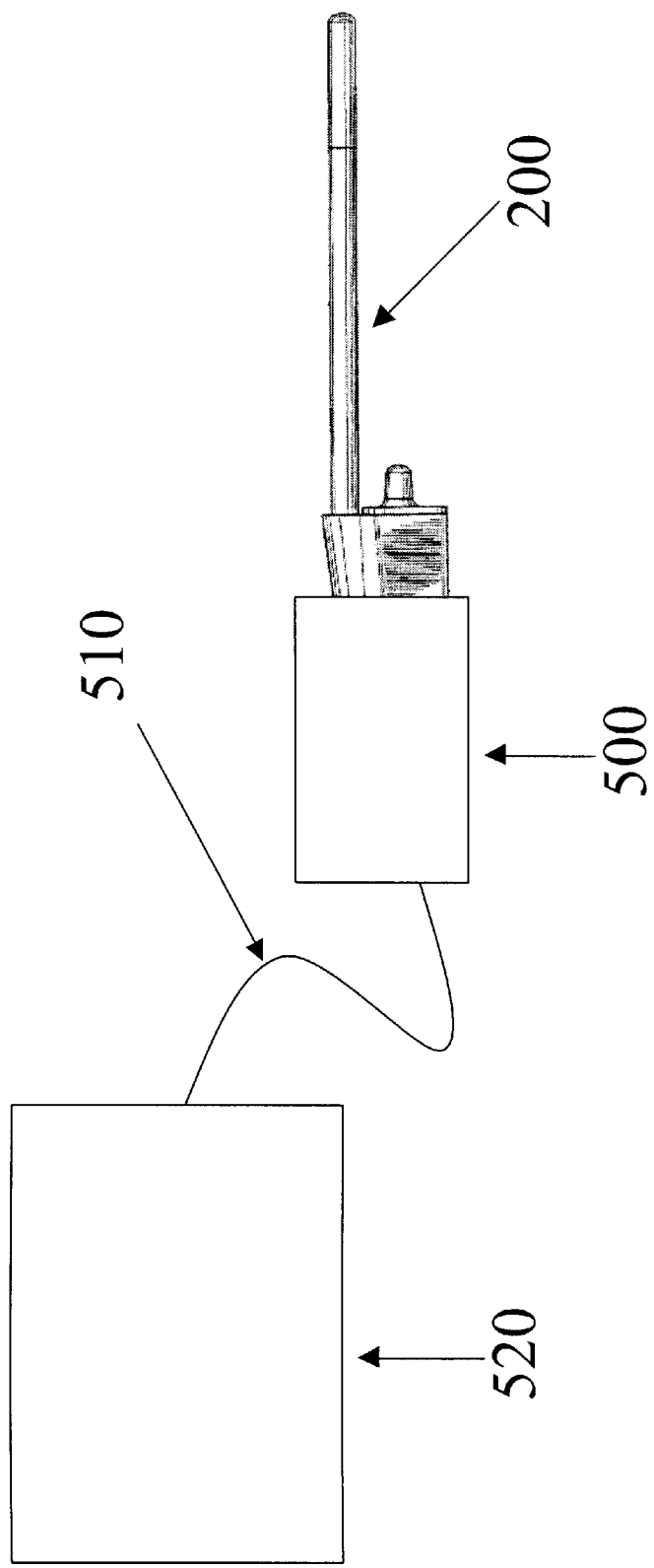
FIG. 15 shows an artificial finger according to the present invention used in association with a finger receptor, which is operatively connected to a non-invasive monitoring device.

Referring now to FIG. 9, 10 and 11, another embodiment of an artificial member according to the present invention is illustrated. In particular, the artificial member is also intended to represent an artificial finger 200 for use in association with a finger receptor 500, which is operatively connected through connection 510 to a non-invasive monitoring device 520 such as a spectrophotometer, as shown in FIG. 15.

The artificial finger 200 of FIGS. 9,10, and 11 is comprised of a handle 290, which may be prepared from aluminum or any other material that is rigid and has strength characteristics. The handle 290 has a tip 300, which is used to connect the handle 290 to the artificial member 210 at 230. The artificial member 210 is comprised of a material that provides a scattering effect similar to tissue such as the skin or a digit. Such materials may include, for example, Teflon®-PTFE; although any other material, such as, for example, Fluorosint™ or Teflon®-PTFE comprising from about 0.1 to about 25% glass fibers, that is capable of providing such a scattering effect is suitable. The member has a hollow or chamber-like portion 220 that determines the amount of internal scattering based on the material filling the cavity. The exact dimensions of the chamber are selected to achieve a spectrum of absorption similar to that observed of a natural finger. More than one chamber may be used.

The chamber 220 acts as a container to hold water or other solutions that are being used as part of the artificial member 210. Also placed within the chamber 220, for the purposes of replicating absorbance of a finger are O-cello materials commonly available as sponge 260 (for example, but not limited to SCOTCH BRITE®) and which is shaped to fit into the chamber 220. The chamber 220 may also be filled with gel materials that hold light scattering materials such as TiO$_2$ or polystyrene nanospheres.

A stopper 270 made of rubber or other suitable material, is fashioned to fit into and seal the top open end of the chamber 220. The stopper 270 may be inserted or removed by gripping the stub 280. A plunger or "stabilizing member" 240 (preferably made of 303 Stainless Steel or other material that is rigid and has strength characteristics) may press fit into mating cavity 250, located in the top of the artificial member 210, and is held in place by an interference fit between the two parts. The purpose of the interlocking plunger 240 is to provide exact placement and holding of the artificial member 210 when inserted into a finger receptor that is operatively connected to a non-invasive monitoring device. The stabilizing member 240, when the artificial member is inserted into the finger receptor mates with a corresponding hole precisely place in the finger receptor just for this purpose, allowing for exact and accurate placement of the artificial member 210 each time it is inserted into the finger receptor. It should be noted however, that other types of "stabilizing members" are envisioned, that may also be used to register the artificial member 210 within the finger receptor.

These parts and their interrelationship are easily seen with reference to FIG. 11, which provides a side view of the artificial finger 200 and illustrates the components in place.

Figure 12:
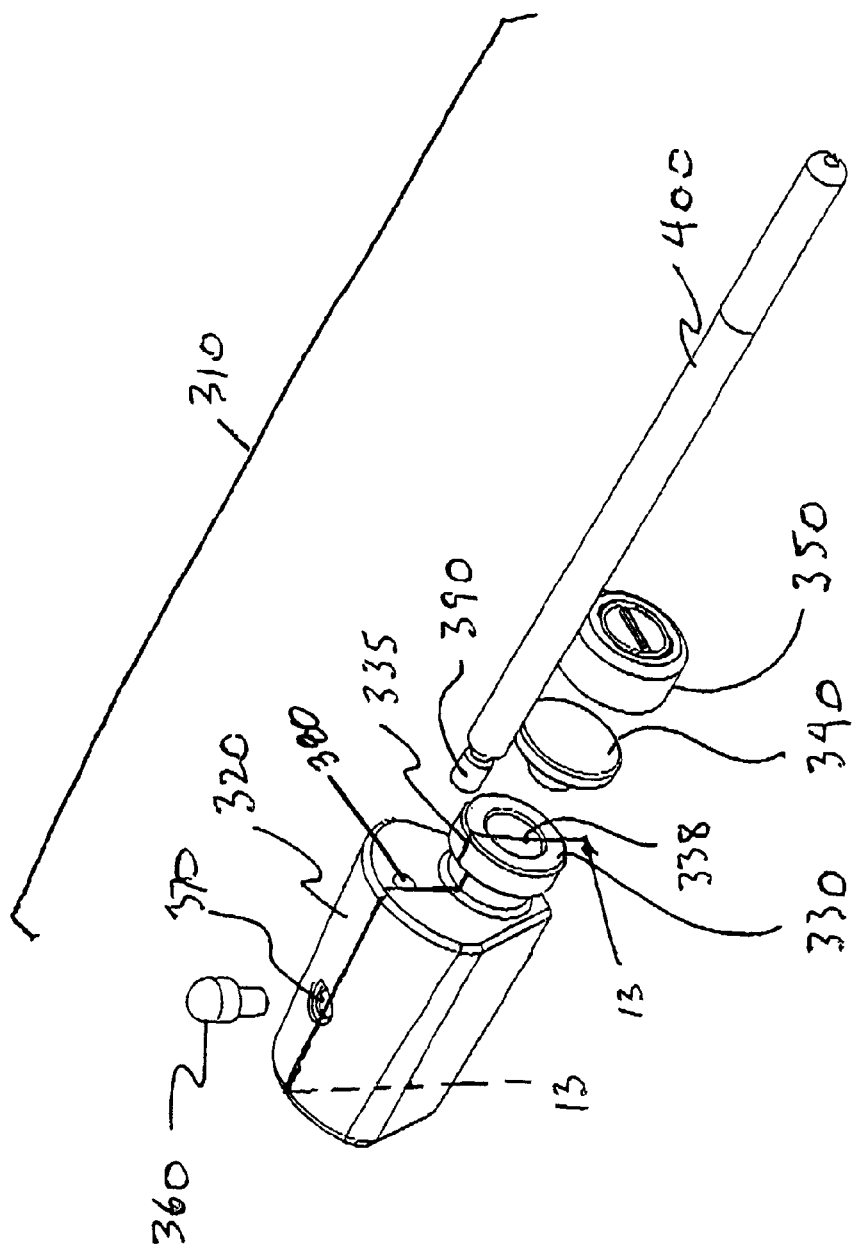
FIG. 12 is an isometric exploded view of a further embodiment of an artificial member according to the present invention in a configuration for use with a finger receptor.
Figure 13:
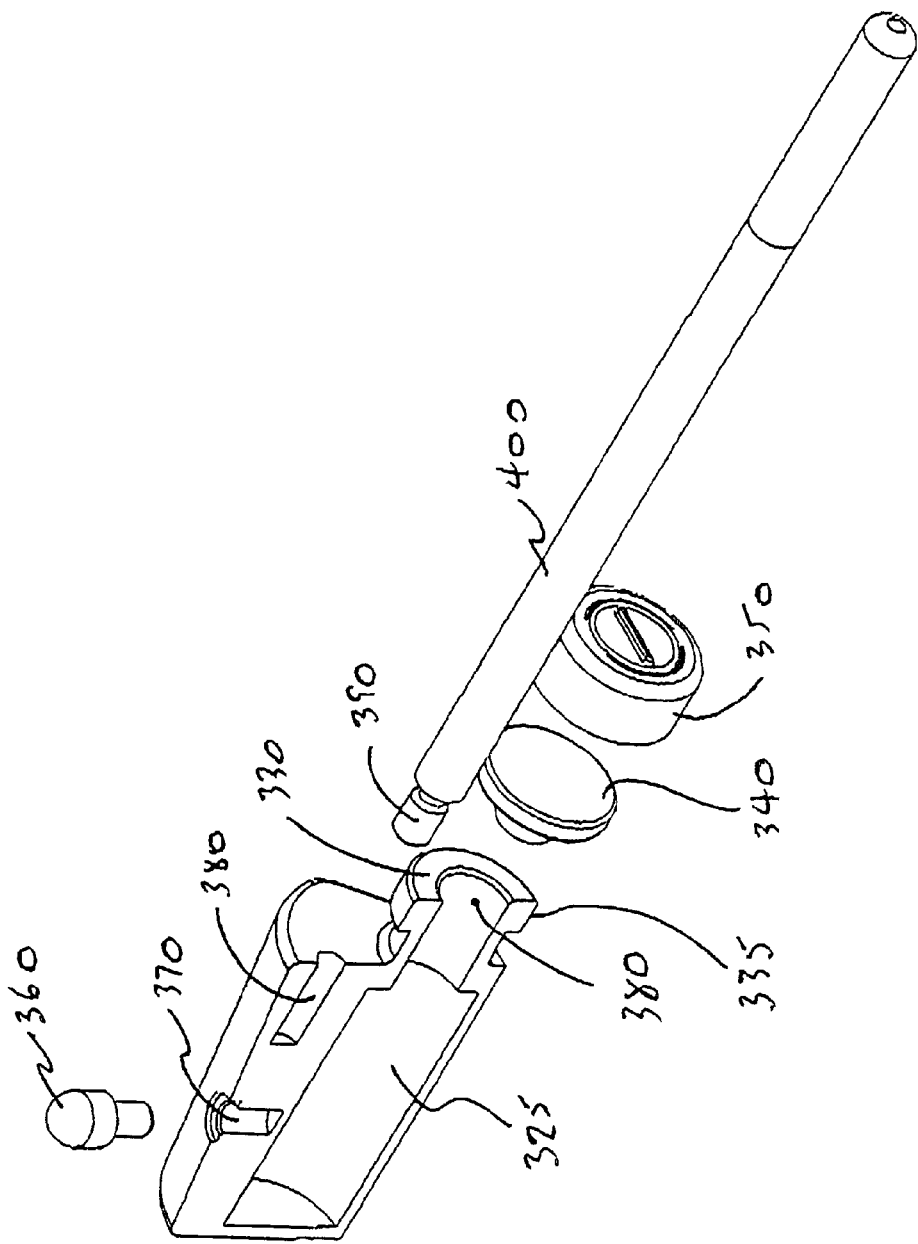
FIG. 13 is a partial section of the artificial member shown in FIG. 12 taken along the line 13—13.
Figure 14:
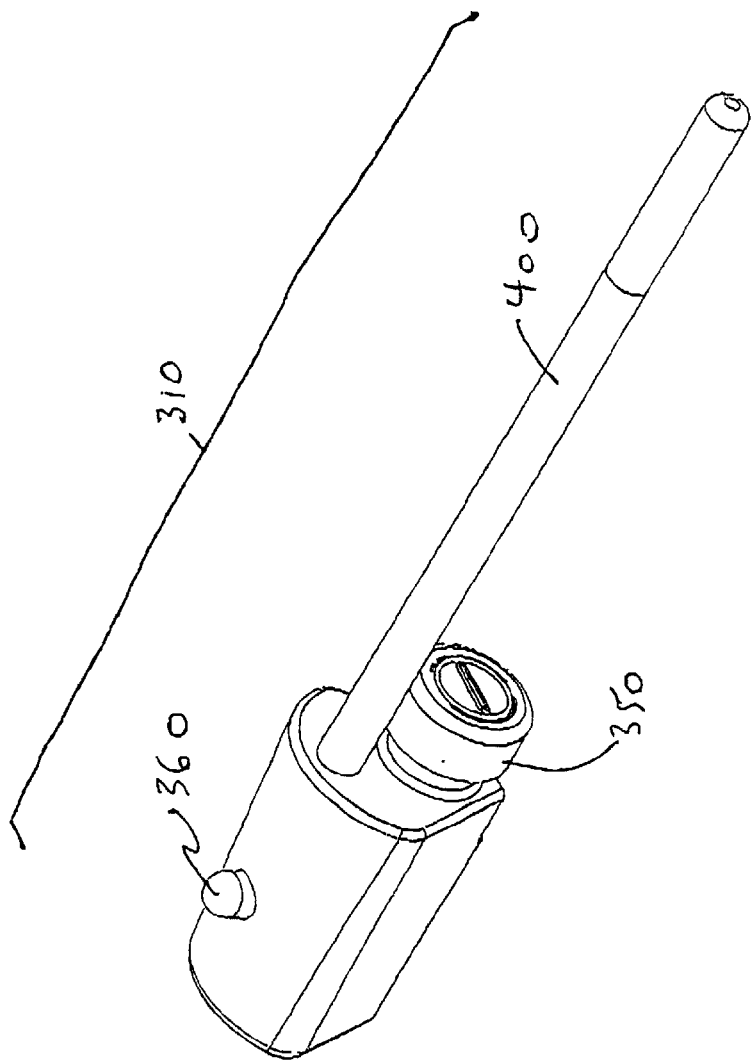
FIG. 14 is an isometric view of an assembled member of FIGS. 12 and 13.

Referring now to FIGS. 12, 13 and 14, another embodiment of an artificial member according to the present invention is illustrated. In particular, this artificial member is also intended to represent an artificial finger for use in association with a finger receptor that is operatively connected to a non-invasive monitoring device such as a spectrophotometer.

The artificial finger 310 of FIGS. 12, 13 and 14 comprises a handle 400, that may preferably be prepared from aluminum or other such material that is rigid and has strength characteristics. The handle 400 has a tip 390, that is used to connect the handle 400 to the artificial member 320 at 380. The artificial member 320 is made of a material that provides a scattering effect similar to tissue such as the skin or a digit. Such materials may include, for example, Teflon®-PTFE; although other materials, such as, for example, Fluorosint™ or Teflon®-PTFE comprising from about 0.1 to about 25% glass fibers, that are capable of providing such a scattering effect is suitable. Preferably, the artificial member 310 is made of Teflon®-PTFE with from about 0.1% to about 5% glass fiber.

The member 310 has a hollow or chamber-like portion 325 that determines the amount of internal scattering based on the material filling the cavity. The exact dimensions of the chamber are selected to achieve a spectrum of absorption similar to that observed of a natural finger. More than one chamber may be used.

The chamber 325 acts as a container to hold water or other solutions that are being used as part of the artificial member 320. Also placed within the chamber 325, for the purposes of replicating absorbance of a finger are O-cello materials commonly available as sponge 260 (for example, but not limited to SCOTCH BRITE®) and which is shaped to fit into the chamber 325. The chamber 325 may also be filled with gel materials that hold light scattering materials such as TiO$_2$ or polystyrene nanospheres.

Furthermore, chamber 325 may be of cylindrical configuration, as shown in FIG. 13. Such a configuration permits a like-sized vial to be inserted into and removed from the chamber 325 as required. The vial would contain desired materials, liquid or solid as described above, to modify the spectral properties of the artificial member 320. Furthermore, the use of a cylindrical chamber allows for varying the diameter and wall thickness of chamber 325.

The artificial member 320 ends in a neck 330 having a lip 335. A septum 340 made of rubber or other suitable material, is fashioned to fit into and seal the open end 338 of neck 330. The skirt of a cap 350 made of aluminum or other deformable material is crimped around lip 335 to retain septum 340 securely over open end 338.

A plunger or "stabilizing member" 360 (preferably made of 303 Stainless Steel or other material that is rigid and has strength characteristics) may press fit into mating cavity 370, located in the top of the artificial member 320, and is held in place by an interference fit between the two parts. The purpose of the interlocking plunger 360 is to provide exact placement and holding of the artificial member 320 when inserted into a finger receptor that is operatively connected to a non-invasive monitoring device. The stabilizing member 360, when the artificial member is inserted into the finger receptor mates with a corresponding hole precisely place in the finger receptor just for this purpose, allowing for exact and accurate placement of the artificial member 320 each time it is inserted into the finger receptor. It should be noted however, that other types of "stabilizing members" are envisioned, that may also be used to register the artificial member 320 within the finger receptor.

These parts and their interrelationship are easily seen with reference to FIG. 14, which provides a view of the assembled artificial finger 310, and illustrates the various components in place.

EXAMPLES

The following non-limiting examples are illustrative of the present invention.

Example 1

Figure 3:
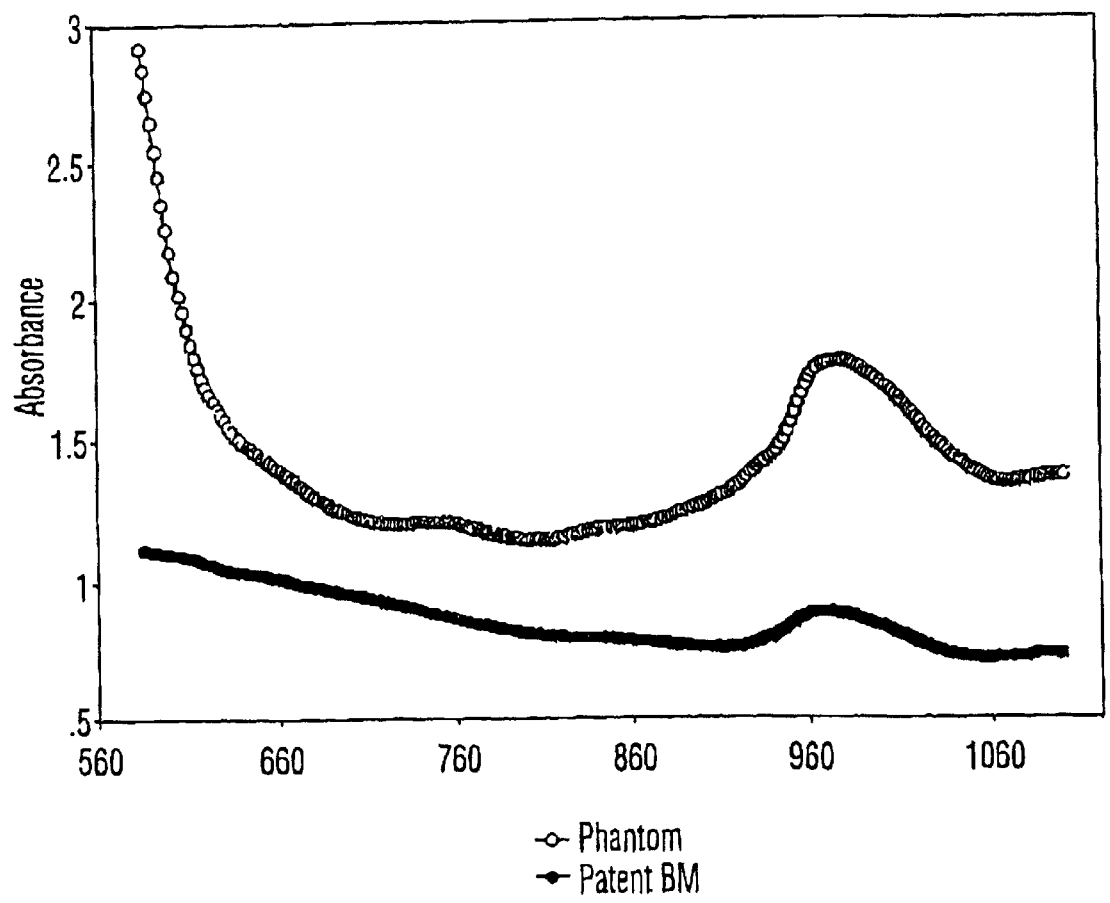
FIG. 3 shows absorbance spectra (580–1100 for water in a subject's finger and an artificial member of the present invention.
Figure 4:
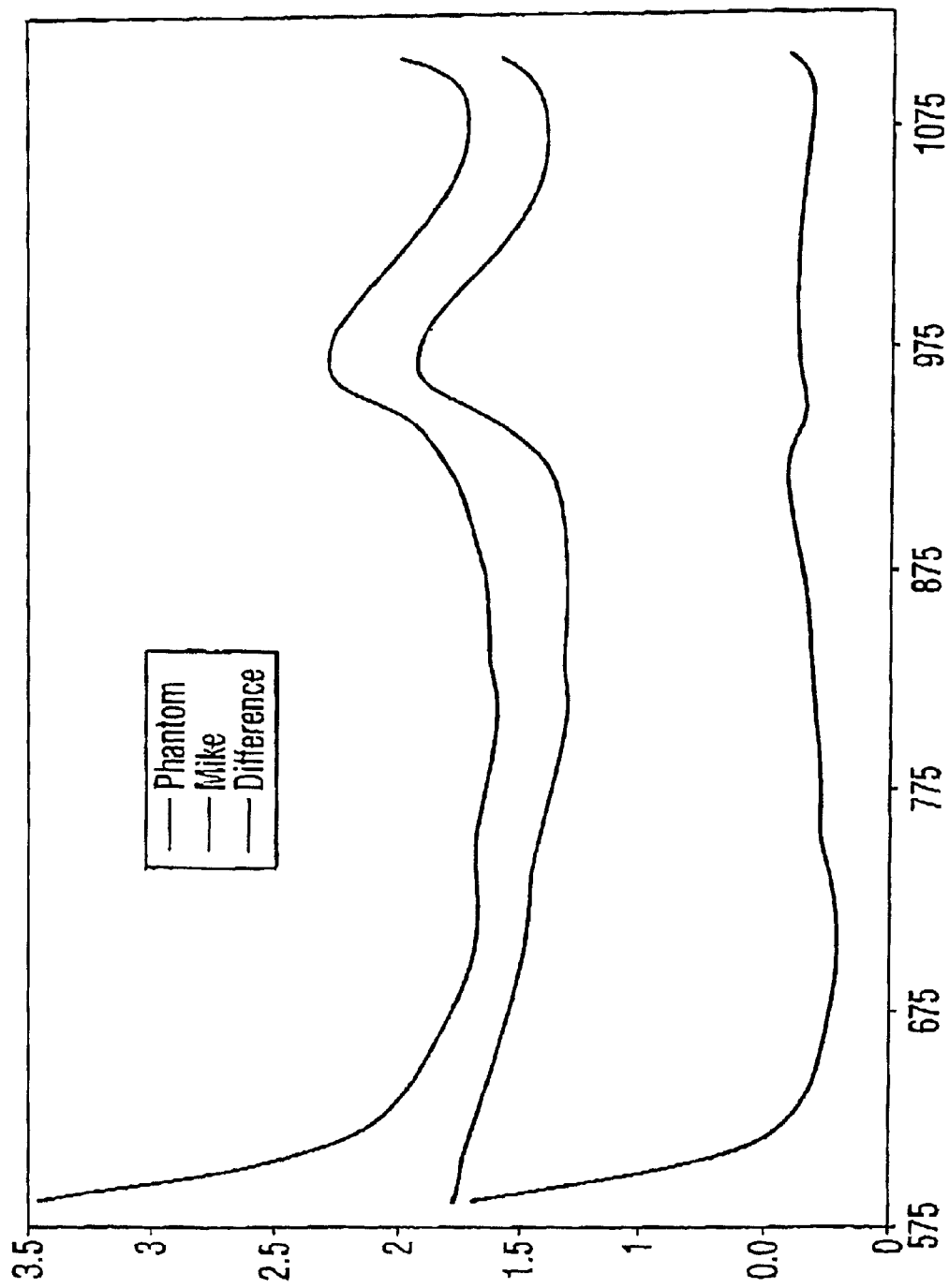
FIG. 4 shows absorbance spectra from 580–1100 nm for a subject's finger and an artificial member as shown in FIG. 3, as well the curve representing the difference between the first two spectra.

An artificial finger made of Teflon®-PTFE was prepared, although as just stated any other highly reflective and light scattering material could have been used. The artificial finger has a hollow portion containing within a further reflective surface, also made of Teflon®PTFE. When filled with water, the artificial finger provides a spectrum somewhat similar to that observed in a normal finger (see, FIG. 3). However, the peak of high absorbance found in the 580 nm region for a normal finger is noticeably missing from the spectrum provided by the artificial finger. Indeed, the different aspects of the artificial finger and a normal finger are illustrated in FIG. 4. As can be seen, the only significant difference resides in the portion of the spectrum peak in the 580 nm region.

Figure 5:
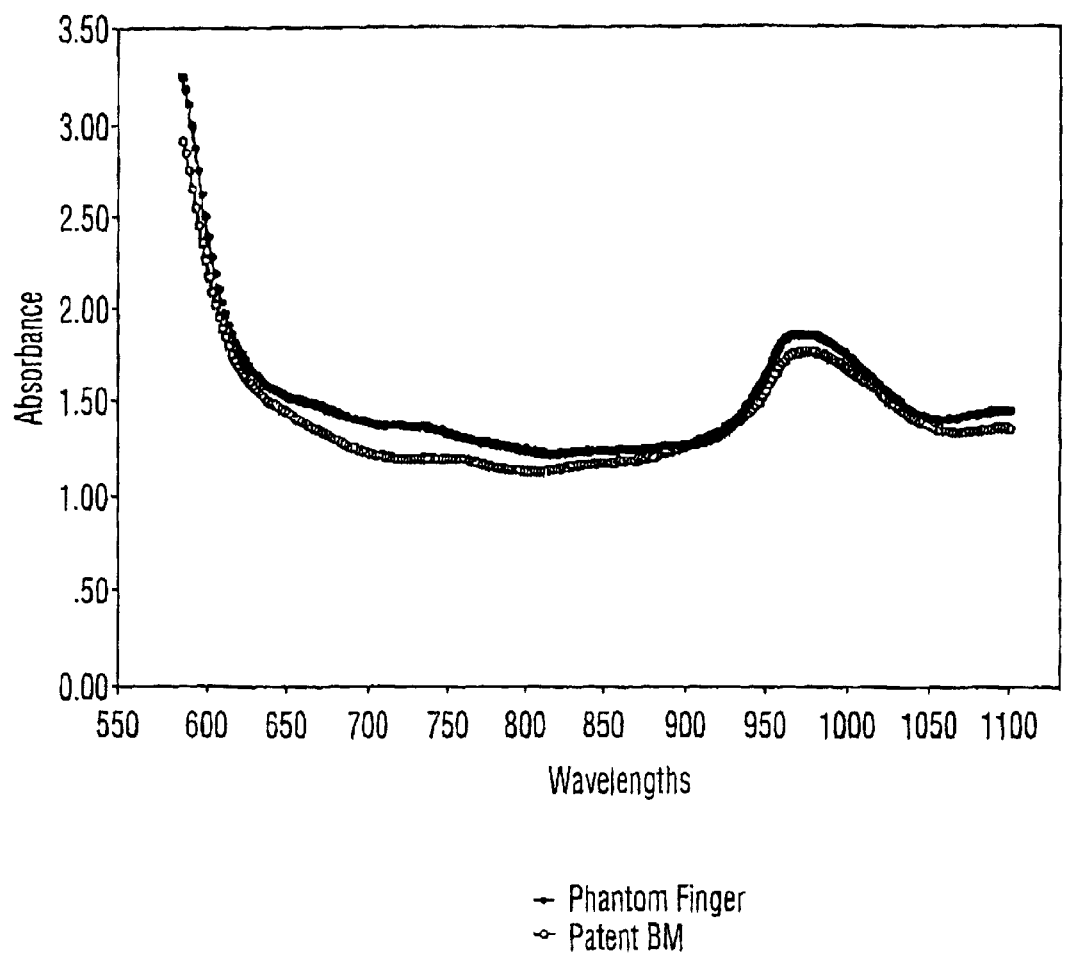
FIG. 5 is absorbance spectra from 580–1100 nm for water in a finger and in an artificial member of the invention wherein the member contains pink sponge (SCOTCH BRITE®, commercially available from 3M, St. Paul, Minn. USA) and water.

To overcome the deficiency of the absorption spectra, various materials were tried, with sponge pads (e.g., SCOTCH BRITE®) and other similar materials providing an absorption spectrum like that of amaranth dye, which is comparable to absorption in a normal human finger. This is shown in FIG. 5. This artificial finger may be used to check the performance of any non-invasive monitoring device that is used to monitor the concentrations of various components of a subject's body parts.

Example 2

An artificial finger made of Teflon®-PTFE was prepared (again, any other highly reflective and light scattering material would have been suitable). The artificial finger has a hollow portion containing within a further reflective surface, also made of Teflon®PTFE. When filled with water, the artificial finger provides a spectrum somewhat similar to that observed in a normal finger (see, FIG. 3). However, the peak of high absorbance found in the 580 nm region for a normal finger is noticeably missing from the spectrum provided by the artificial finger. The different aspects of the artificial finger and a normal finger are illustrated in FIG. 4. Again, the only significant difference resides in the portion of the spectrum peak in the 580 nm region.

To overcome the deficiency of the absorption spectra, various materials were tried, with sponge pads (e.g., SCOTCH BRITE®) and other similar materials providing an absorption spectrum like that of amaranth dye, which is comparable to absorption in a normal human finger. This is shown in FIG. 5. This artificial finger may be used to check the performance of any non-invasive monitoring device that is used to monitor the concentrations of various components of a subject's body parts.

Example 3

Figure 6:
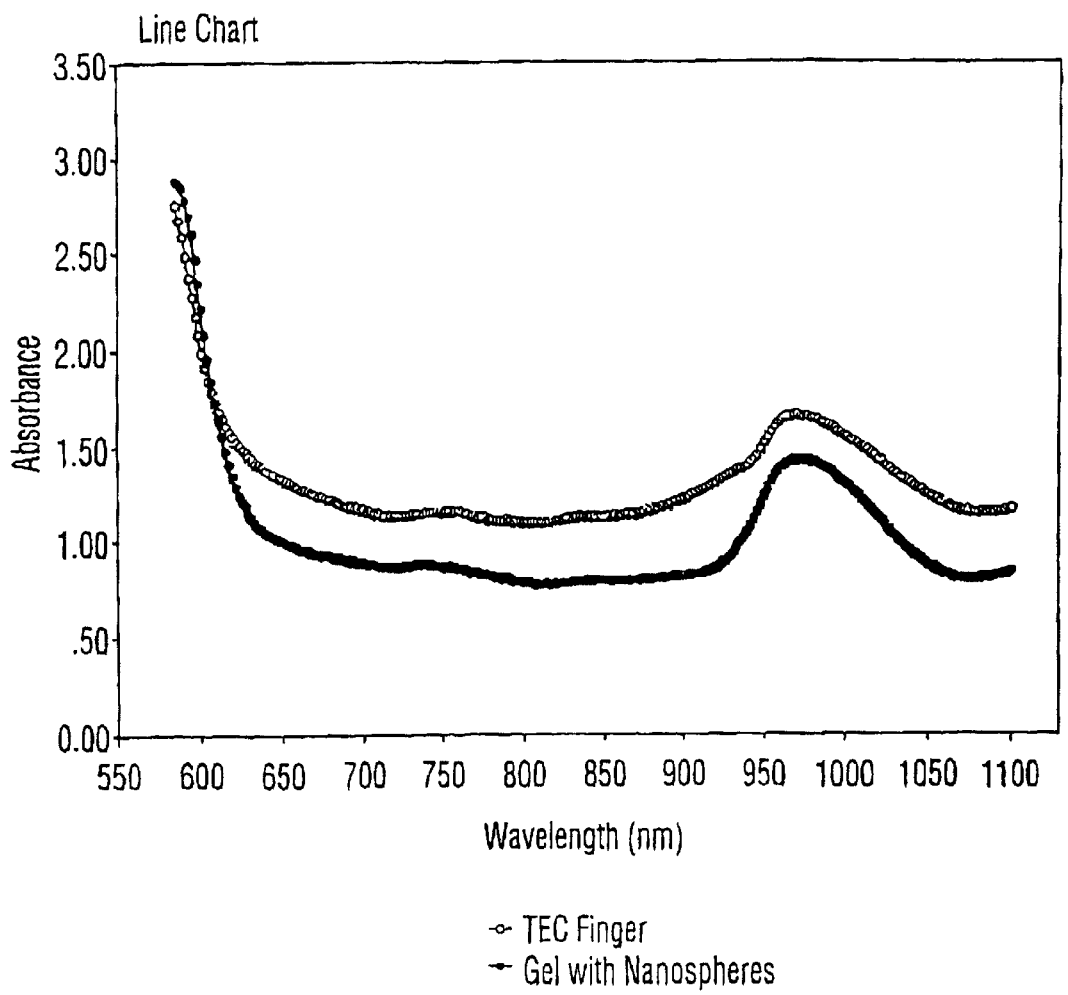
FIG. 6 is absorbance spectra from 580–1100 nm for water in a finger and in an artificial member of the invention wherein the member contains polystyrene nanospheres in water and gelatin, plus amaranth dye and sodium benzoate as a preservative.

An artificial finger made of Teflon®-PTFE was prepared, (again, any other highly reflective and light scattering material would have been suitable). The artificial finger has a hollow portion containing a further reflective surface, also made of Teflon®-PTFE. When filled with water, the artificial finger provides a spectrum somewhat similar to that observed in a normal finger, and the only significant difference resides in the portion of the spectrum peak in the 580 nm region. To overcome the deficiency of the absorption spectra, nanospheres comprising polystyrene in water and gelatin plus amaranth dye, as well as sodium benzoate as a preservative were used. The results are illustrated in FIG. 6.

As is readily apparent from the foregoing disclosure and examples, the artificial finger of the present invention may be used to check the performance of any non-invasive monitoring device that is used to monitor the concentrations of various components of a subject's body parts.

While the present invention has been described with reference to what are presently considered to be preferred examples, it is to be understood that the invention is not limited to these disclosed examples. To the contrary, the invention is intended to cover various modifications and equivalents included within the spirit and scope of the appended claims.

The complete text of any publications, patents and patent applications referred to in this disclosure, is incorporated herein by reference, and just as if the text of each individual document was explicitly and individually incorporated herein by reference.

We claim:

1. An artificial member that simulates an animal body part, the artificial member comprising a container, the container comprising one, or more than one chamber and having a neck extending from end thereof, the neck having a lumen in fluid communication with the one, or more than one chamber, and the neck comprising an orifice sealed with a cap, the orifice in fluid communication with the lumen, wherein the container is made of a light-scattering and light-reflecting material that approximates the light-scattering, light-reflecting and light-absorbing properties of the animal body part.

2. The artificial member of claim 1, further comprising a septum fitting over the orifice and secured by the cap.

3. The artificial member of claim 2, wherein the septum is uniform with the cap.

4. The artificial member of claim 1, wherein the neck further comprises a flange, and the cap is secured about the flange.

5. The artificial member of claim 4, wherein the flange is an annular flange.

6. The artificial member of claim 5, wherein the cap is a crimp cap.

7. The artificial member of claim 5, wherein the cap is made of aluminum.

8. The artificial member of claim 1, wherein the light-scattering and light-reflecting material is Teflon®-PTFE.

9. The artificial member of claim 1, wherein the light-scattering and light-reflecting material is Teflon®-PTFE containing from about 0.1% to about 25% glass fiber.

10. The artificial member of claim 9, wherein the light-scattering and light-reflecting material is Teflon®-PTFE containing from about 0.1% to about 5% glass fiber.

11. The artificial member of claim 1, wherein the artificial member simulates a human finger.

12. The artificial member of claim 1, wherein the container comprises a single chamber.

13. The artificial member of claim 1, wherein the container comprises two chambers.

14. The artificial member of claim 1, wherein the one, or more than one chamber is cylindrical in shape.

15. The artificial member of claim 1, wherein the one, or more than one chamber is filled with an O-cellulose material that simulates the light scattering properties of tissue.

16. The artificial member of claim 1, wherein the one, or more than one chamber is filled with a gel material containing amaranth dye and sodium benzoate and holding light scattering and reflective particles that simulate the light scattering properties of body tissue.

17. The artificial member of claim 16, wherein the reflective particles comprise Teflon®-PTFE, $TiO_2$ or polystyrene nanospheres.

18. The artificial member of claim 1, further comprising a stabilizing member extending from the container to reversibly urge surfaces of the artificial member into contact with a measuring receptor that is operatively connected to a non-invasive monitoring device.

19. A method of determining the precision and accuracy of a non-invasive monitoring device comprising:
   (a) providing an artificial member comprising a container, the container comprising one, or more than one chamber, and having a neck extending from one end thereof, the neck having a lumen in fluid communication with the one, or more than one chamber and the neck comprising an orifice sealed with a cap, the orifice in fluid communication with the lumen wherein the container is made of a light-scattering and light-reflecting material that approximates the light-scattering, light-reflecting and light-absorbing properties of an animal body part;
   (b) inserting the artificial member into a measuring receptor that is operatively connected to the non-invasive monitoring device;
   (c) taking measurements with the monitoring device; and
   (d) comparing the measurements obtained in step (c) with measurements obtained with the animal body part, which the artificial member simulates.

20. The method of claim 19, wherein the artificial member provided in step (a) further comprises a septum fitting over the orifice and being secured by the cap.

21. The method of claim 20, wherein the septum of the artificial member provided in step (a) is uniform with the cap.

22. The method of claim 21, wherein the neck of the artificial member provided in step (a) further comprises a flange, and wherein the cap is secured over the flange.

23. The method of claim 22, wherein the neck flange of the artificial member provided in step (a) is an annular flange.

24. The method of claim 23, wherein the cap of the artificial member provided in step (a) is a crimp cap.

25. The method of claim 24, wherein the cap of the artificial member provided in step (a) is formed of aluminum.

26. The method of claim 19, wherein the light-scattering and light-reflecting material of the artificial member provided in step (a) is Teflon®-PTFE.

27. The method of claim 19, wherein the light-scattering and light-reflecting material of the artificial member provided in step (a) is Teflon®-PTFE containing from about 0.1% to about 25% glass fiber.

28. The method of claim 27, wherein the light-scattering and light-reflecting material of the artificial member provided in step (a) is Teflon®-PTFE containing from about 0.1% to about 5% glass fiber.

29. The method of claim 19, wherein the artificial member simulates a human finger.

* * * * *